United States Patent [19]

Martin

[11] Patent Number: 5,284,875

[45] Date of Patent: * Feb. 8, 1994

[54] FORTIFIED QUARTERNARY AMMONIUM COMPOUND WITH DUAL SYNERGISTIC PHENOLS

[76] Inventor: Howard Martin, 1106 Spring St., Silver Spring, Md. 20910

[*] Notice: The portion of the term of this patent subsequent to Jan. 8, 2008 has been disclaimed.

[21] Appl. No.: 47,947

[22] Filed: Apr. 16, 1993

Related U.S. Application Data

[63] Continuation-in-part of Ser. No. 243,088, Sep. 12, 1988, Pat. No. 4,983,635.

[51] Int. Cl.$^5$ ................... A61K 31/14; A61K 31/045
[52] U.S. Cl. .................................. 514/643; 514/642; 514/724; 514/728
[58] Field of Search ................ 514/643, 642, 724, 728

[56] References Cited

PUBLICATIONS

Chemical Abstract 84:17445a (1976), Washman et al.
Chemical Abstract 90:1014c (1978), Poli et al.
The Merck Index, Tenth Edition, p. 1043 (1983).
The Merck Index, Tenth Edition, p. 749 (1983).

Primary Examiner—Zohreh A. Fay
Attorney, Agent, or Firm—Walter G. Finch

[57] ABSTRACT

A fortified quaternary ammonium compound with and without dual synergistic phenols is provided for disinfection and sanitization. One formula consists of dual chain quaternary ammonium chloride (N-alkyl dimethylethylbenzyl ammonium chloride and N-alkyl dimethylbenzyl ammonium chloride), ortho phenyl phenol, para tertiary amyl phenol, citric or acetic acid, sodium citrate, isopropyl or ethyl alcohol, triethanol amine-HCl and water in the following proportions 50.00 to 0.50 grams, 1.00 to 0.08 grams, 1.00 to 0.08 grams, 0.50 to 0.05 grams, 0.25 to 0.025 grams, 14.00 to 1.40 grams, 5.00 to 1.00 grams, 28.25 to 96.865 grams. The formula for environmentally protected uses consists of dual chain quaternary ammonium chloride (N-alkyl dimethylethylbenzyl ammonium chloride and N-alkyl dimethylbenzyl ammonium chloride), citric or acetic acid, sodium citrate, isopropyl or ethyl alcohol, triethanol amine-HCl and water in the following proportions: 50.00 to 0.50 grams, 0.50 to 0.05 grams, 0.25 to 0.025 grams, 14.00 to 1.40 grams, 5.00 to 1.00 grams, 30.25 to 97.525 grams. These formulas are the concentrated formulations and can be diluted for use in the health professions, consumer areas, and agricultural areas.

2 Claims, No Drawings

FORTIFIED QUATERNARY AMMONIUM COMPOUND WITH DUAL SYNERGISTIC PHENOLS

BACKGROUND AND SUMMARY OF THE INVENTION

This application is a continuation in part of Ser. No. 07/243,088, filed Sep. 12, 1988, now U.S. Pat. No. 4,983,635.

This application is an improvement over U.S. Pat. No. 4,983,635 issued on Jan. 8, 1991 to Howard Martin.

This invention relates to proper infection control through mandatory chemical disinfection of instrumentation, and more particularly to a new formulation for disinfection and sanitization of surfaces, instruments, hospitals, and homes, convalescent and other similar material and the like.

Proper infection control, through chemical disinfection, of instrumentation is mandatory. In light of current knowledge, many compounds that were used in the past are no longer deemed acceptable. However, if these compounds were to be fortified and recombined into a new combination, rather than standing alone, the positive qualities would lead to a synergistic compound and then lead to a new useful efficacious disinfectant.

The most popular compound in use presently is glutaraldehyde. There are several drawbacks to glutaraldehyde in chemical disinfection usage. They are expensive, can only be diluted to a 1.0% if acidic or 2.0% if alkaline. They are considered relatively toxic at 1.0% and toxic at 2.0% in handling. They cause severe dermatitis and are allergenic. They have been shown to be unreliable in killing mycobacterium tuberculosis (TB). Some forms require heating to be effective and thereby give rise to noxious fumes. The shelf-life, once mixed, is not more than 30 days for the popular alkaline forms.

In contrast, quaternary ammonium compounds, alcohols and phenols have been studied and used for a long time and are less expensive and toxic as well as odorless. Individually, phenols have been in disfavor and alcohols are merely mid-level disinfectants. Quaternary ammonium compounds (QUATS) were used for disinfection for many years but certain limitations have caused them to fall into disuse.

However QUATS possess a high surface activity. Natural hard water reduced their effectiveness and gram negative organisms were found to be resistant. This water problem is overcome by preparation with distilled water and a special additive triethanol amine HCl. Irregular effectiveness against TB is overcome by the phenols and alcohols.

A new poly dual chain substituted quaternary ammonium compound has been found to be a more effective formulation but is still considered, if used alone, insufficient as a high level disinfectant. This poly dual chain, a homologous series of alkyl dimethyl ethyl benzyl ammonium chloride, has been shown to have the highest cidal efficiency against test organisms for approval by the U. S. Environmental Protection Agency.

Other positive qualities of QUATS are that they maintain activity against most other gram positive organisms. They are less expensive than many other disinfectants. QUATS are relatively nontoxic and allergic reactions are rare and they are odorless. They do not cloud instruments with lenses nor etch metal instruments. The QUATS have been used against viruses and have special properties against these organisms. They are very stable and have a long shelf-life. Recent testing has indicated that a higher concentration of QUAT will inactivate gram negative organisms. QUATS will also behave as a surfactant enabling other compounds to penetrate microorganisms with greater effectiveness, thereby enhancing the secondary compounds cidal or killing effect.

Alcohols, as a group, possess many desirable features for a disinfectant. Its negatives have been quick evaporation and erratic cidal effects. The positive are the cleaning action, bactericidal effects against vegetative organisms and are inexpensive.

Alcohols work by denaturing the proteins of the microorganisms. Pure alcohol is not as effective as mixtures of alcohol plus water. It also interferes with cellular metabolism preventing cell division. Isopropyl alcohol is the alcohol of choice due to lack of government restriction and also being the highest molecular weight alcohol miscible with water.

Isopoopyl alcohol bactericidal effects are slightly greater than ethyl alcohol. Against mycobacterium tuberculosis, isopropyl alcohol was as effective as ethyl alcohol at one third the concentration. Isopropyl alcohol is also effective against lipophilic viruses.

The phenols were originally the standard disinfectant, but with improved compounds, they have not played a significant role. Overlooked have been the phenols effectiveness against certain microorganisms. These variations in their anti-bacterial behavior and toxicity have led to the development of synthetic compounds. Phenols act as protoplasmic poisons, penetrating and interrupting the cell wall and precipitating out cellular proteins. Eventually, cell death occurs from the inactivation of essential cell enzyme systems.

Two new phenol derivations are ortho phenyl phenol and para tertiary amyl phenol. They have higher molecular weights and show a higher degree of bactericidal effectiveness and a decrease in toxicity. Ortho phenyl phenol is approximately ten times more effective than standard phenol and is water soluble. It is also a fungicide and tuberculocide.

Para tertiary amyl phenol is a high level bactericide but is relatively insoluble in water. If it can be solubilized and stabilized, it is 400 times as effective as standard phenol against gram positive and 50 times more effective against gram negatives as well as being a fungicide.

A properly formulated phenolic disinfectant can be diluted with hard water and maintain complete clarity and germicidal activity. The effect of pH is particularly noticeable when phenols are solubilized. Control of pH, through the use of citric acid or acetic acid to develop an acidic solution, results in a highly efficient preparation of phenols with excellent disinfectant and detergent properties. Such a product will efficiently clean and disinfect in operation at a lower cost.

The development of a spray, squeeze bottle. or wipe is a logical extension of the formulation and would provide a simple means for use in a small or difficult access areas. When sprayed or wiped wet, a surface is readily and conveniently disinfected. The properly formulated phenols are non-specific in regard to fungicidal and bactericidal action.

This new formulation allows the para tertiary amyl phenol to remain in solution for up to two years. Phenolics have great value in specific areas. Improper combinations of phenols and anionic surfactants will show variations in cidal effects. The addition of alcohol and pH control to stabilize the formula has been determined by experimentation in order to give a stable acidic pH.

It is an object of this invention to provide a high level disinfectant that is reliable and economical to the health profession, industry, agriculture and consumer areas.

Tests were performed to show the effectiveness of three (3) lots of the fortified quaternary ammonium compound in concentrate form as a disinfecting solution at an exposure time of three (3) minutes. AOAC Methods and EPA DSS/TSS methods were used to perform these tests with the quaternary ammonium compound diluted at 1:128. A summary of the results are as follows:

| Test Organism | Exposure Time | Carrier Type | No. of Growth/ Total No. of Tubes |
|---|---|---|---|
| S. choleraesuis | 3 min. | SS | 0/180 |
| s. aureus | 3 min. | SS | 0/100 |
| Ps. aeruginosa | 3 min. | SS | 0/180 |
| T. mentagrophytes | 3 min. | SS | 0/40 |
| M. bovis | 40 min. | Logarithmic Reduction Method | |

Further tests were performed to determine the tuberculocidal activity of the fortified quaternary ammonium compound. These tests were conducted according to AOAC Methods. A summary of the results are as follows:

| Product | Lot # | Results | | |
|---|---|---|---|---|
| | | MPB[1] | Kir.[2] | TB[3] |
| Kwik Kill 5000[4] | 9/13/88 | 10− | 10− | 10− |
| Kwik Kill 2500[5] | 9/13/88 | 10− | 10− | 10− |
| Controls | | 10+ | 10+ | 10+ |

[1]MBP - Modified Proskauer-Beck Broth
[2]Kir. - Kirchner Medium
[3]TB - TB Broth Base
[4]Kwik Kill 5000 is a tradename for the fortified quaternary ammonium compound.
[5]Kwik Kill 2500 is a tradename for the fortified quaternary ammonium compound.

| Phenol Resistance of M. Bovis ATCC 19015 | | | |
|---|---|---|---|
| Phenol Concentration | MBP[1] | Kir.[2] | TB[3] |
| 1-50 | 10− | 10− | 10− |
| 1-75 | 10+ | 10+ | 10+ |

[1]MBP - Modified Proskauer-Beck Broth
[2]Kir - Kirchner Medium
[3]TB - TB Broth Base Another object of this invention is to combine positive qualities of QUATS, alcohol, and phenols into a highly synergistic new solution that overcomes the weaknesses of the individual compounds.

And another object of this invention is to provide a new formulation for disinfection and sanitization which is concentrated and can be diluted for use in the health professions, consumer areas, and agricultural areas.

Tests were performed comparing the cidal effect of the fortified quaternary ammonium compounds to other disinfectants of the same general category. Shown here are the results of tests of the product that best compared with the quaternary ammonium compound. The fortified quaternary ammonium compound (Kwikkill) at a dilution of 1:50 initial quaternary ammonium concentration equals that of the undiluted comparison product (Quat A) and the alcohol content was 5% higher in the Quat A than in Kwikkill.

| Test Organism | Time (min.) to Kill Test Organism at Given Dilution | | | | | |
|---|---|---|---|---|---|---|
| | Kwikkill[1] | | | Quat A[2] | | |
| | 1:128 | 1:265 | 1:512 | 1:2 | 1:5 | 1:10 |
| Quat % | .20 | .10 | .05 | | | |
| P. aeruginosa | 2 | 5 | 10 | 5 | 10 | 20 |
| S. aureus | 2 | 5 | 10 | 10 | 10 | 20 |
| S. choleraesuis | 1 | 5 | 10 | 5 | 10 | 20 |
| M. bovis | nt. | 10 | 20 | 10 | 15 | nt. |

[1]Kwikkill = fortified quaternary ammonium compound with dual phenolics
[2]Quat A = alcohol quaternary ammonium product

| Phenol Coefficients of Fortified Quaternary Ammonium v. Standard Phenol | | |
|---|---|---|
| | Phenol Coefficient | |
| Test Organism | Kwikkill[1] | Quat A[2] |
| S. aureus | 8.5 | 0.03 |
| S. choleraesuis | 5.7 | 0.06 |
| P. aeruginosa | 6.4 | 0.06 |
| M. bovis | 5.1 | 0.04 |

[1]Kwikkill = fortified quaternary ammonium compound with dual phenols
[2]Quat A = alcohol quaternary ammonium product

| Effectiveness of Fortified Quaternary Ammonium Compound at an Exposure Time of 3 Minutes | | | |
|---|---|---|---|
| Test Organism | Exposure Time | Carrier Type | No. of Growths/ Total No. of Tubes |
| S. choleraesuis | 3 min | SS | 0/180 |
| S. aureus | 3 min | SS | 0/100 |
| Ps. aeruginosa | 3 min | SS | 0/180 |
| T. mentagrophytes | 3 min | SS | 0/40 |
| M. bovis | 40 min | Logarithmic Reduction Method | |

Even another object of this invention is to provide a concentrated formulation in which the variant can be decreased in quaternary ammonium concentration from the concentrate of 25to a low of 0.5%, with all other compounds remaining the same.

It is the purpose of this formulation to develop a high level, disinfectant that is reliable and inexpensive to the health professions, industry, agriculture and consumer areas. The purpose of this new formulation is to combine the positive qualities of the aforementioned QUATS. alcohol, and phenols into a highly synergistic new solution that overcome the weaknesses of the individual components.

The dual chain quaternary ammonium compounds+isopropyl or ethyl alcohol+ortho phenyl phenol+-para tertiary amyl phenol+citric or acetic acid+-sodium citrate+triethanol amine-HCl will give rise to a compound that is superior to the individual components, superior to older dual phenols and superior to glutaraldehyde.

Usage in a high concentration will enable ease of shipping dilution as needed, no activation, low toxicity, and a wide range of cidal effects. In a high concentration, the compound can prevent proleferation of bacteria in injection water used in oil secondary recovery systems.

In proper concentrations, the new formulation will inhibit the sulfate reducing bacteria and pseudomonas species that contaminate the wells and holding tanks of oil systems. The compound can also be formulated as a solution properly concentrated for immersion of instruments, as a spray, as a wipe, as a solution to be activated in an ultrasonic bath.

A new formulation for disinfection and sanitization composed as follows:

| | |
|---|---|
| Dual quaternary ammonium chloride (N-alkyl dimethylethylbenzyl ammonium chloride) (N-alkyl dimethylbenzyl ammonium chloride) | 50.00 to 0.50 grams |
| Para tertiary amyl phenol | 1.00 to 0.08 grams |
| Ortho phenyl phenol | 1.00 to 0.08 grams |
| Citric or acetic acid | 0.50 to 0.05 grams |
| Sodium citrate | 0.25 to 0.025 grams |
| Isopropyl or ethyl alcohol | 14.00 to 1.40 grams |
| Triethanol amine-HCl | 5.00 to 1.00 grams |
| Water | 28.25 to 96.865 grams |

Formulation without the phenols for environmental uses in industrial areas which prohibit the use of phenols, comprised as follows:

| | |
|---|---|
| Dual quaternary ammonium chloride (N-alkyl dimethylethylbenzyl ammonium chloride) (N-alkyl dimethylbenzyl ammonium chloride) | 50.00 to 0.50 grams |
| Citric or acetic acid | 0.50 to 0.05 grams |
| Sodium citrate | 0.25 to 0.025 grams |
| Isopropyl or ethyl alcohol | 14.00 to 1.40 grams |
| Triethanol amine-HCl | 5.00 to 1.00 grams |
| Water | 75.25 to 97.475 grams |

This formula represents an improvement over the formula in U.S. Pat. No. 4,983,635, in that also with the addition of triethanol amine-HCl improves the formula's ability to remain in solution in hard water. The hard water problem of over 420 ppm has been the main reason the dual chain QUATS have not been greatly used in some areas of the country. Also, the addition of acetic acid eliminates the stickiness of the formula's residue. These two improvements make the formula more useable.

An additional change is the inclusion of formulations which do not use phenols. This change makes those formulations appropriate for environmental protection from phenol contamination in restricted areas for industrial uses.

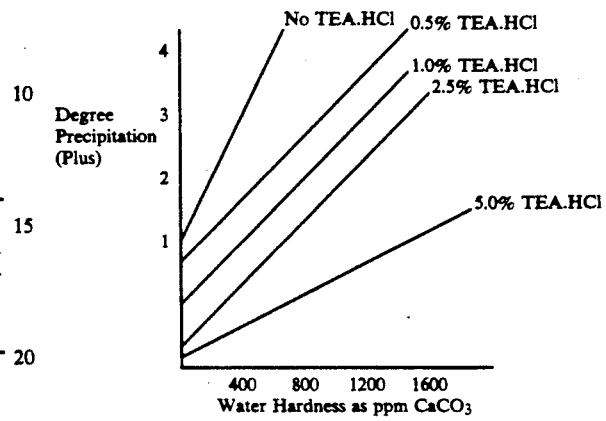

TABLE I

| | | BACTERIAL KILL TIMES AND CONCENTRATIONS | | | | |
|---|---|---|---|---|---|---|
| PRODUCT | DILUTION | WATER HARDNESS | CONTACT TIME | S. AUREUS | S. CHLERAESUIS | P. AERUGINOSA |
| Kwikkill 191923 | 1:64 | 0 ppm | 3 minutes | 20/20 | 20/20 | 20/20 |
| Kwikkill 191923 | 1:64 | 400 ppm | 3 minutes | 20/20 | 20/20 | 20/20 |
| Kwikkill 191923 | 1:128 | 0 ppm | 3 minutes | 20/20 | 20/20 | 19/20 |
| Kwikkill 191923 | 1:128 | 400 ppm | 3 minutes | 20/20 | 19/20 | 20/20 |
| Kwikkill 191923 | 1:256 | 0 ppm | 3 minutes | 20/20 | 20/20 | 18/20 |
| Kwikkill 191923 | 1:256 | 400 ppm | 3 minutes | 20/20 | 19/20 | 19/20 |
| Kwikkill 191923 | 1:256 | 400 ppm | 2 minutes | 19/20 | 18/20 | 16/20 |
| Kwikkill 191923 | 1:128 | 400 ppm | 2 minutes | 19/20 | 20/20 | 18/20 |
| Kwikkill 191923 | 1:64 | 400 ppm | 2 minutes | 20/20 | 20/20 | 20/20 |

TABLE II

| | BACTERIALCIDAL KILL OF TB (M. bovis) | | | |
|---|---|---|---|---|
| PRODUCT | DILUTION | WATER HARDNESS | CONTACT TIME | M. BOVIS |
| Kwikkill 191922 | 1:64 | 400 ppm | 3 minutes | 05/20 |
| Kwikkill 191922 | 1:64 | 400 ppm | 10 minutes | 17/20 |
| Kwikkill 191922 | 1:64 | 400 ppm | 15 minutes | 20/20 |
| Kwikkill 191922 | 1:64 | 400 ppm | 20 minutes | 20/20 |
| Kwikkill 191922 | 1:128 | 400 ppm | 3 minutes | 06/20 |
| Kwikkill 191922 | 1:128 | 400 ppm | 10 minutes | 14/20 |
| Kwikkill 191922 | 1:128 | 400 ppm | 15 minutes | 18/20 |
| Kwikkill 191922 | 1:128 | 400 ppm | 20 minutes | 18/20 |
| Kwikkill 191922 | 1:128 | 0 ppm | 3 minutes | 03/20 |
| Kwikkill 191922 | 1:128 | 0 ppm | 10 minutes | 15/20 |
| Kwikkill 191922 | 1:128 | 0 ppm | 15 minutes | 18/20 |
| Kwikkill 191922 | 1:128 | 0 ppm | 20 minutes | 20/20 |

What is claimed is:

1. A new formulation for disinfection and sanitization, comprising,

| | |
|---|---|
| Dual chain quaternary ammonium chloride (N-alkyl dimethylethylbenzyl ammonium chloride) (N-alkyl dimethylbenzyl ammonium chloride) | 50.00 to 0.50 grams |
| Para tertiary amyl phenol | 1.00 to 0.08 grams |
| Ortho phenyl phenol | 1.00 to 0.08 grams |
| Citric or acetic acid | 0.50 to 0.05 grams |
| Sodium citrate | 0.25 to 0.025 grams |
| Isopropyl or ethyl alcohol | 14.00 to 1.40 grams |
| Triethanol amine-HCl | 5.00 to 1.00 grams |
| Water | 28.25 to 96.865 grams |

2. A new formulation for disinfection and sanitization, comprising,

| | |
|---|---|
| Dual Quaternary ammonium chloride | 50.00 to 0.50 grams |
| (N-alkyl dimethylethylbenzyl ammonium chloride) | |
| (N-alkyl dimethylbenzyl ammonium chloride) | |
| Citric or acetic acid | 0.50 to 0.05 grams |
| Sodium citrate | 0.25 to 0.025 grams |
| Isopropyl or ethyl alcohol | 14.00 to 1.40 grams |
| Triethanol amine-HCl | 5.00 to 1.00 grams |
| Water | 30.25 to 97.525 grams |

* * * * *